(12) United States Patent
Smith et al.

(10) Patent No.: US 9,329,112 B2
(45) Date of Patent: May 3, 2016

(54) CONTAINER STORING FREEZE-DRIED BIOLOGICAL SAMPLE

(75) Inventors: Michael John Smith, Cardiff (GB); Stevan Paul Tortorella, Wells, ME (US)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 150 days.

(21) Appl. No.: 13/982,312

(22) PCT Filed: Jan. 25, 2012

(86) PCT No.: PCT/EP2012/051098
§ 371 (c)(1),
(2), (4) Date: Jul. 29, 2013

(87) PCT Pub. No.: WO2012/101150
PCT Pub. Date: Aug. 2, 2012

(65) Prior Publication Data
US 2013/0323715 A1    Dec. 5, 2013

(30) Foreign Application Priority Data
Jan. 28, 2011    (GB) .................................. 1101488.3

(51) Int. Cl.
*G01N 1/42* (2006.01)
*B01L 3/00* (2006.01)

(52) U.S. Cl.
CPC . *G01N 1/42* (2013.01); *B01L 3/508* (2013.01); *B01L 2200/0647* (2013.01);
(Continued)

(58) Field of Classification Search
CPC .................... B01L 2200/0647; B01L 2200/16; B01L 2300/06; B01L 2300/0829; B01L 2300/0832; B01L 3/502; B01L 3/508; B01L 3/52; G01N 1/42; Y10T 436/25; Y10T 436/2525

USPC .......... 436/174, 176; 422/500, 547, 549, 554, 422/557, 558, 559, 560, 561, 562; 435/283.1, 288.1, 288.2, 4
See application file for complete search history.

(56) References Cited

U.S. PATENT DOCUMENTS 4,073,693 A * 2/1978 Janin ................................ 435/37
4,235,839 A   11/1980 Vesterberg
(Continued)

FOREIGN PATENT DOCUMENTS

GB        983311     2/1965
JP    2003-177092 A  6/2003
(Continued)

OTHER PUBLICATIONS

JP Office Action for JP Application No. 2013-543128 mailed Nov. 30, 2015 (6 pages).

*Primary Examiner* — Maureen Wallenhorst
(74) *Attorney, Agent, or Firm* — Sutherland Asbill & Brennan LP (57) ABSTRACT

A container holding, and a method of storing, freeze-dried biological samples. The container includes a chamber having an upper portion and a lower portion. The chamber includes a wall, and the lower portion of the chamber is fluidly connected to the upper portion of the chamber such that, when liquid is received at the upper portion, the received liquid can pass to and accumulate in the lower portion. Further, the freeze-dried material is located in the lower portion, and the container includes a physical structure in the form of a stop protruding inwards from the wall, the physical structure being for inhibiting the freeze-dried material from moving from the lower portion of the chamber to the upper portion of the chamber.

17 Claims, 10 Drawing Sheets

(52) U.S. Cl.
CPC ......... *B01L 2200/16* (2013.01); *B01L 2300/06* (2013.01); *B01L 2300/0829* (2013.01); *B01L 2300/0832* (2013.01); *Y10T 436/2525* (2015.01)

(56) References Cited

U.S. PATENT DOCUMENTS

| | | |
|---|---|---|
| 4,720,374 A | 1/1988 | Ramachandran |
| 5,120,503 A | 6/1992 | Hinckley et al. |
| 5,650,125 A | 7/1997 | Bosanquet |
| 6,793,885 B1 | 9/2004 | Yokoi et al. |
| 7,138,091 B2 | 11/2006 | Lee et al. |
| 2003/0108447 A1 | 6/2003 | Yokoi et al. |
| 2006/0013727 A1 | 1/2006 | Rudloff |
| 2007/0054301 A1* | 3/2007 | Becker et al. ............ 435/6 |
| 2009/0136385 A1* | 5/2009 | Handique et al. .......... 422/102 |

FOREIGN PATENT DOCUMENTS

| | | |
|---|---|---|
| JP | 2008-298615 A | 12/2008 |
| JP | 2010-117222 A | 5/2010 |
| WO | WO 02/45859 | 6/2002 |

\* cited by examiner

CONTAINER STORING FREEZE-DRIED BIOLOGICAL SAMPLE

CROSS-REFERENCE TO RELATED APPLICATIONS

This application is a filing under 35 U.S.C. 371 of international application number PCT/EP2012/051098, filed Jan. 25, 2012, published on Aug. 2, 2012 as WO 2012/101150, which claims priority to 1101488.3 filed in Great Britain on Jan. 28, 2011.

FIELD OF THE INVENTION

The present invention relates to containers for holding and methods for storing freeze-dried biological samples.

BACKGROUND OF THE INVENTION

Biological samples, such as tissue or cellular extracts or lysates, enzymes, proteins, peptides, nucleic acids, fatty acids, glycerides, carbohydrates, oligosaccharides and saccharides, are commonly prepared at a first site, stored in a container, and transported to a second site for processing. One example of this is in diagnostic devices and/or in DNA/RNA amplification processes. This may require that the biological sample, which may be an enzyme such as a polymerase or reverse transcriptase, is stored for significant periods of time in the container and/or subject to vibrations and/or other external forces during transportation.

A convenient way of supplying such biological samples is to freeze-dry the biological sample in the container prior to transportation. The container is typically a tube of cylindrical cross-section having a single internal chamber. The freeze-drying process typically involves freezing a liquid sample, reducing the ambient pressure, and then gradually adding enough heat to allow sublimation of the water contained within the frozen liquid. The result is a coagulated, dehydrated sample formed at the bottom of the container; the container is then sealed and the biological sample (which may contain an enzyme) is stored, and transported, in this freeze-dried state.

When the biological sample is subsequently required for processing, it can be reconstituted by adding water to the freeze-dried material. The amount of biological sample dissolved for a given volume of water added can be critical; for example, if the amount of biological sample dissolved is too small, the strength of the solution may be insufficient.

However, it has been observed that when the freeze-dried material is supplied in existing tubes, some of the freeze-dried material remains un-dissolved when water is subsequently added. This can result in a solution of insufficient strength, as mentioned above.

Furthermore, biological samples freeze-dried, stored and transported in this way are often of high value; accordingly, un-dissolved biological sample is wasteful and can increase costs.

It is an object of the present invention to at least mitigate some of the problems of the prior art.

SUMMARY OF THE INVENTION

In accordance with a first aspect of the present invention, there is provided a container holding a freeze-dried material comprising a biological sample, the container comprising a chamber having an upper portion and a lower portion, the chamber comprising a wall and the lower portion being fluidly connected to the upper portion such that, when liquid is received at the upper portion, the received liquid can pass to and accumulate in the lower portion, wherein the freeze-dried material is located in said lower portion, and the container comprises a physical structure protruding inwards from the wall, the physical structure being for inhibiting the freeze-dried material from moving from the lower portion of the chamber to the upper portion of the chamber, and wherein the freeze-dried material defines a first cross-section and the physical structure comprises a stop extending inwards from an internal wall of said chamber, thereby defining a second cross-section, the second cross-section having a dimension smaller than a corresponding dimension of the first cross-section.

Since the freeze-dried material is inhibited from moving out of the lower portion of the chamber, it can be contained within a given volume, ensuring that when the material is subsequently reconstituted by the insertion of a liquid into the container, all of the freeze-dried material can be dissolved in the liquid, ensuring that the reconstituted solution is of the required strength. Further, since a physical structure is used to prevent the movement of the freeze-dried material, the use of a chemical, such a bonding agent, which may interfere with the composition of the reconstituted material can be avoided.

In addition, because the chamber has upper and lower portions, with the freeze-dried material being kept in the lower chamber, the freeze-dried material can be kept away from any seal applied to the upper portion; this avoids the contamination which may result from such contact.

Alternatively or additionally, in some embodiments the freeze-dried material defines a first cross-section and the physical structure comprises a stop extending inwards from an internal wall of said chamber, the stop defining a second cross-section, the second cross-section having a dimension smaller than a corresponding dimension of the first cross-section. The stop may define a boundary between the upper portion of the chamber and the lower portion of the chamber. The stop may thus define a volume of the container within which the freeze-dried material is maintained. In some embodiments, the stop comprises a collar that is integrally formed with the chamber. Alternatively, the stop may comprise a movable insert, the movable insert being movable within said chamber, thereby varying the extent or position of said boundary. Using a movable collar enables the volume of the chamber within which the freeze-dried material is maintained to be varied.

Preferably, the container comprises a physical structure comprising a textured surface, which further increases the bonding surface area between the freeze-dried biological sample and the chamber.

The container may be of a plastics material.

The chamber may have a substantially circular cross-section.

Preferably, the upper portion extends from a first end of the container, and the container comprises a seal at the first end.

In accordance with a second aspect of the present invention, there is provided an apparatus storing a freeze-dried material comprising a biological sample, the apparatus comprising: a plurality of containers according to the first aspect of the invention; and a base plate supporting the plurality of containers.

The apparatus may comprise a base plate of a plastics material.

In accordance with a third aspect of the present invention, there is provided a method of storing a biological sample, comprising: providing a container, the container comprising a chamber having an upper portion and a lower portion, the chamber comprising a wall and the lower portion being fluidly connected to the upper portion such that, when liquid is received at the upper portion, the received liquid can pass to and accumulate in the lower portion; inserting a material containing a biological sample into the chamber and accumulating the liquid biological sample in the lower portion of the chamber; and performing a freeze-drying process on the material, whereby a freeze-dried material comprising said biological sample is formed in the lower portion, wherein the container comprises a physical structure protruding inwards from the wall, the physical structure being for inhibiting the freeze-dried material from moving out of the lower portion, and wherein the freeze-dried material defines a first cross-section and the physical structure comprises a stop extending inwards from an internal wall of said chamber, thereby defining a second cross-section, the second cross-section having a dimension smaller than a corresponding dimension of the first cross-section.

In accordance with a fourth aspect of the present invention, there is provided a container holding a freeze-dried biological sample, the container comprising a chamber having an upper portion and a lower portion, the lower portion comprising a wall and being fluidly connected to the upper portion such that, when liquid is received at the upper portion, the received liquid can pass to and accumulate in the lower portion, wherein the freeze-dried biological sample is located in said lower portion, and the wall comprises a rough surface to which the freeze-dried biological sample is bonded, whereby the freeze-dried biological sample is prevented from moving from the lower portion to the upper portion.

A further aspect of the invention provides the use of the container of the first aspect, and/or the array of the second aspect, and/or the container of the fourth aspect for processing a biological sample.

Further features and advantages of the invention will become apparent from the following description of preferred embodiments of the invention, given by way of example only, which is made with reference to the accompanying drawings.

DETAILED DESCRIPTION OF THE INVENTION

Figure 1:
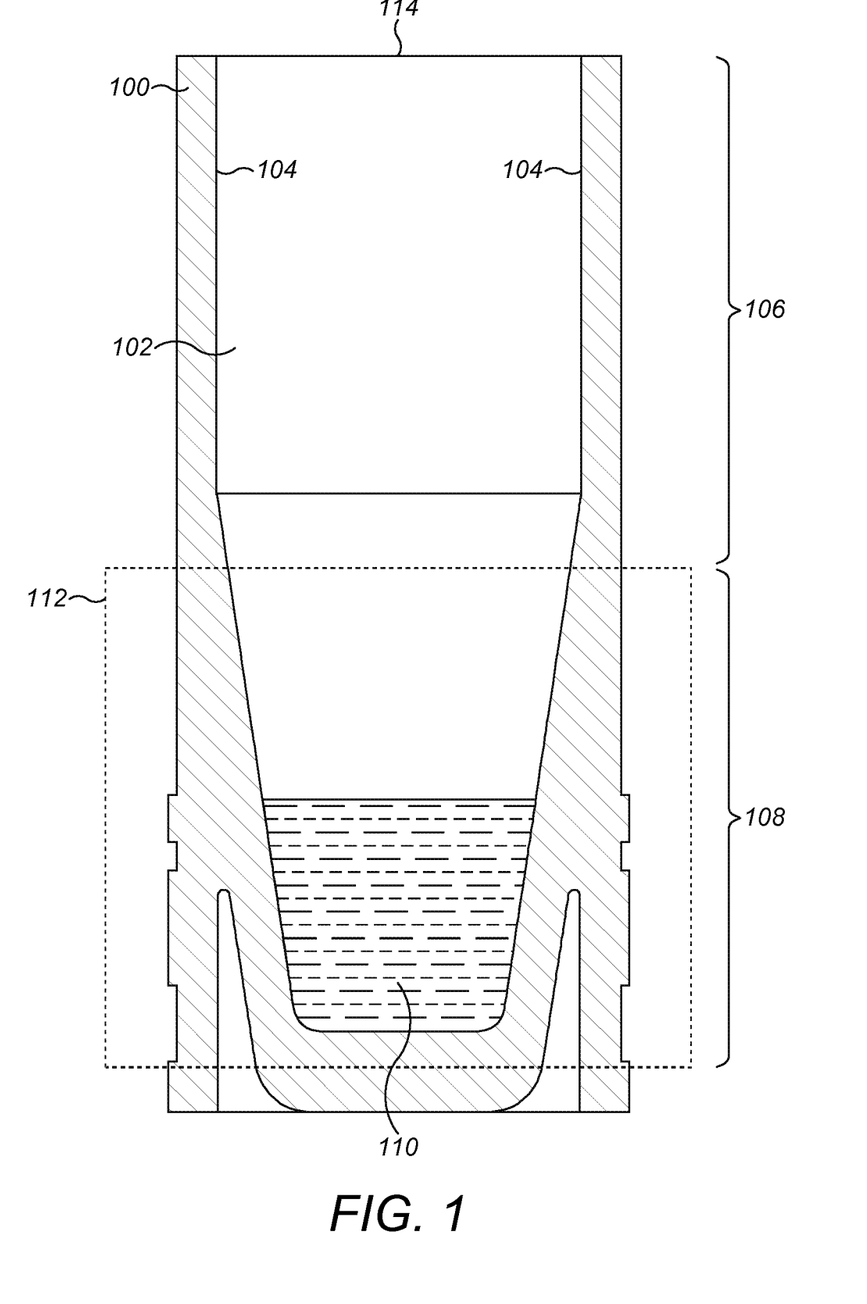
FIG. 1 shows a cross-section view of a container holding a freeze-dried material.

In FIG. 1, a container in the form of a tube 100 is provided, the tube 100 comprising a chamber 102 having a wall 104, an upper portion 106, and a lower portion 108, the lower portion 106 holding a freeze-dried material comprising a biological sample; the freeze-dried material is hereinafter referred to as a cake 110. Typically, the cake 110 is in a disc-shaped form. The tube 100 comprises a physical structure 112 to inhibit movement of the freeze-dried biological sample from the lower portion 108 of the chamber 102 to the upper portion 106 of the chamber 102. The tube 100 comprises a first end 114, which may initially be open in order to enable insertion of the material prior to freeze-drying, and subsequently closed with a seal (not shown).

The external dimensions of the tube 100 may be fixed at an industry standard for ease of handling, for example, automated handling by existing laboratory equipment. Typically, the tube 100 is 8 mm in diameter and 18.3 mm long. Typically, the internal dimensions of the tube are large enough in both diameter and depth to accommodate standard dispensing tools, for example pipetting needles in automated dispensing systems; this has the advantage that there is no need for readjustment or calibration of existing tools.

The biological sample may comprise an enzyme, such as a polymerase, reverse transcriptase or any other enzyme, blood, tissue, serum or any other biological substance.

Figure 2A:
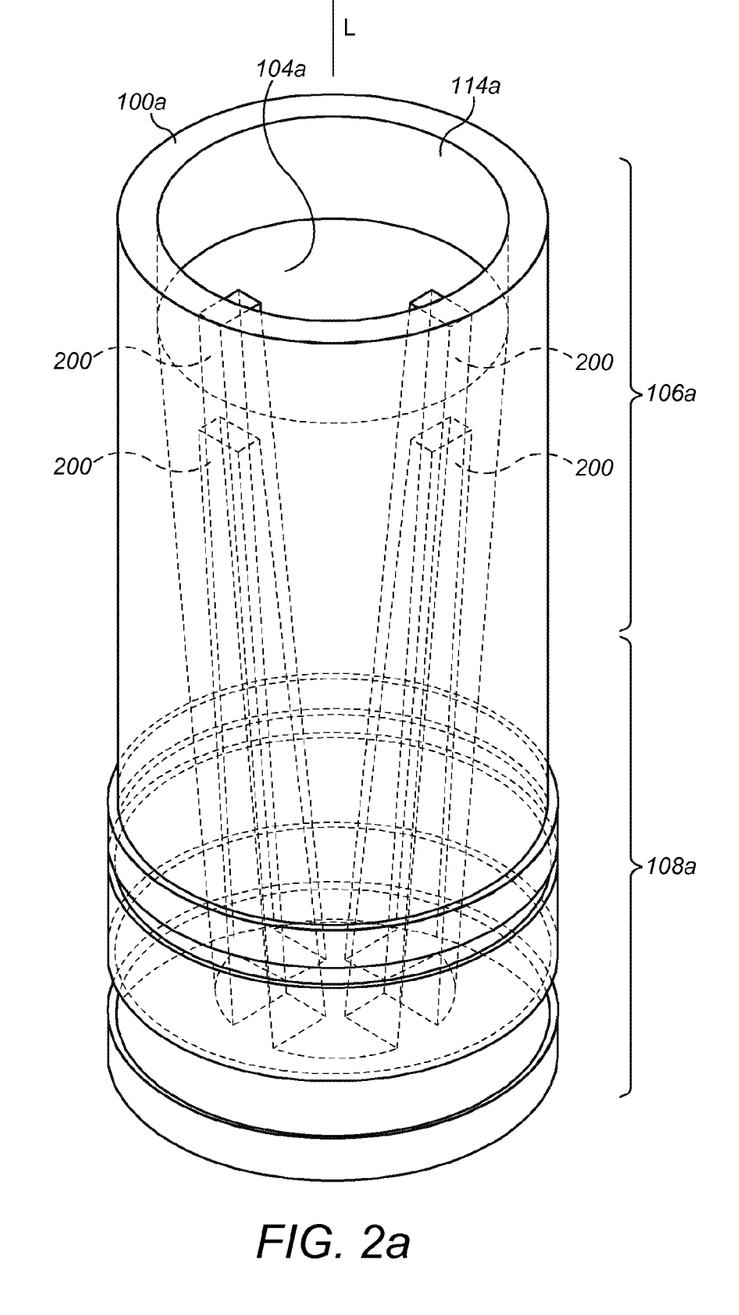
FIG. 2a shows a perspective view of another container for holding a freeze-dried material.
Figure 2B:
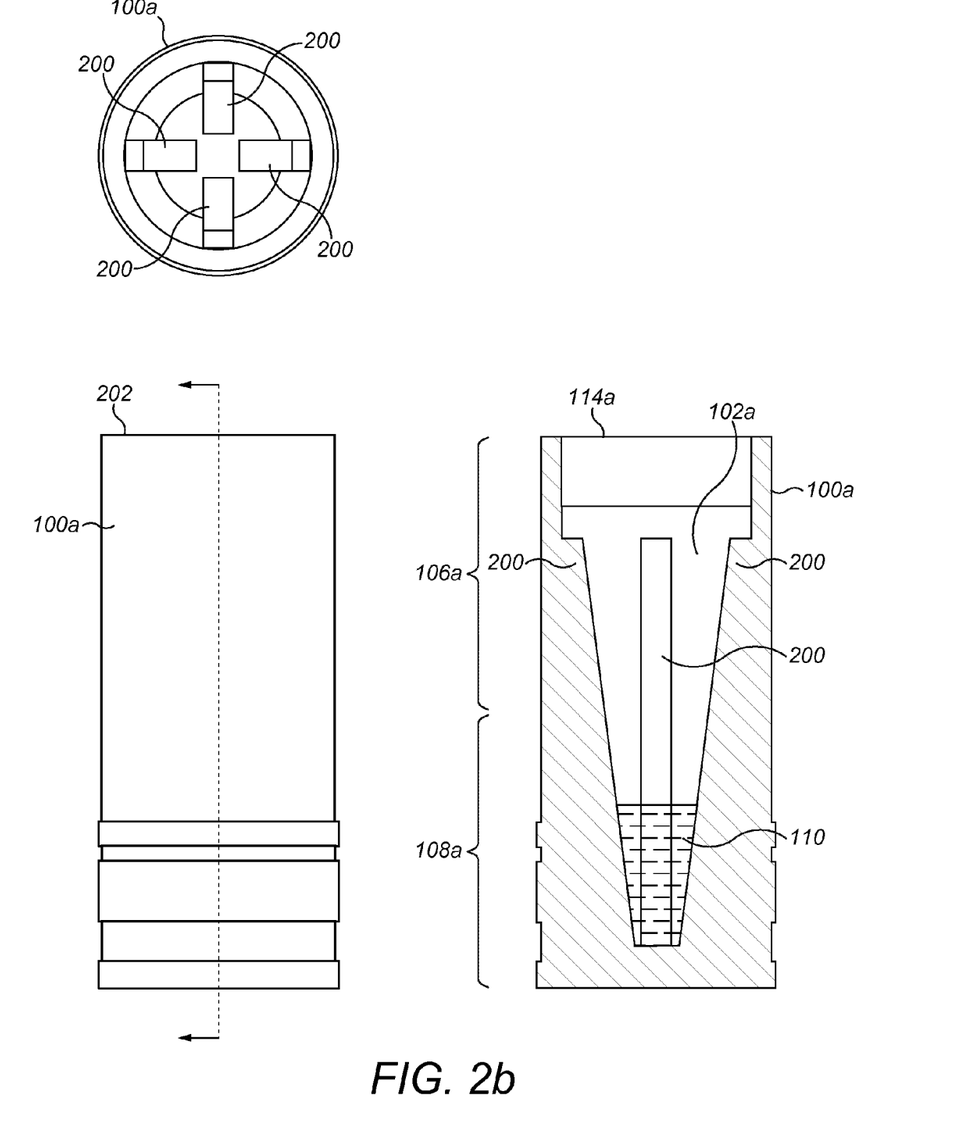
FIG. 2b shows orthographic projections of the container of FIG. 2a holding a freeze-dried material.

In FIGS. 2a and 2b, a tube 100a is provided in which a physical structure 112 in the form of protrusions, herein referred to as fins 200, extends inwards from the wall 104a of the chamber 102a, and extends longitudinally along a direction parallel to the axis L of the tube 100a.

FIG. 2a shows the tube 100a prior to insertion of the biological sample. The tube 100a is initially open at a first end 114a, from which the upper portion 106a extends. During preparation, a material (typically in liquid form) containing the biological sample, is inserted into the chamber 102a via the first end 114a and allowed to accumulate in the lower portion 108a. A freeze-drying process is then performed so that the material is dehydrated in the lower portion 108a, and in and around the spaces between the fins 200, thereby forming the cake 110 shown in FIG. 2b. The freeze-drying process bonds the cake 110 to the fins 200. The additional contact area between the cake 110 and the internal surface of the tube 100a provided by the fins 200 increases the strength of the bond between the cake 110 and the tube 100a, thereby increasing the ability of the tube 100a to hold the freeze-dried cake 110 in place. Further, the shape of the freeze-dried cake 110 comprises recesses into which the fins 200 fit. This interlocking fit between the freeze-dried cake 110 and the fins 200 prevents rotation of the freeze-dried cake 110 about the central longitudinal axis L of the tube 100a, further reducing the likelihood of detachment.

The first end 114a may be sealed, subsequent to insertion of the material that is to be freeze-dried with a seal (not shown). The seal, which may be an impermeable seal, may be made of flexible foil, polymer laminate and/or any other suitable material, and may be held in place with a permanent or semi-permanent adhesive. When the freeze-dried material is required for subsequent processing, the seal may be removed, or penetrated by a dispensing needle, for example. Since the cake 110 is kept in the lower portion 108a of the chamber 102a, it is kept away from the seal. This is advantageous because contact with the seal can cause contamination of the freeze-dried biological sample.

When the biological sample is subsequently reconstituted, by inserting, for example, water into the tube 100a, provided that sufficient volume of water is inserted to fill the lower portion 108b, it can be ensured that substantially all of the cake 110 is dissolved in the water.

Figure 3A:
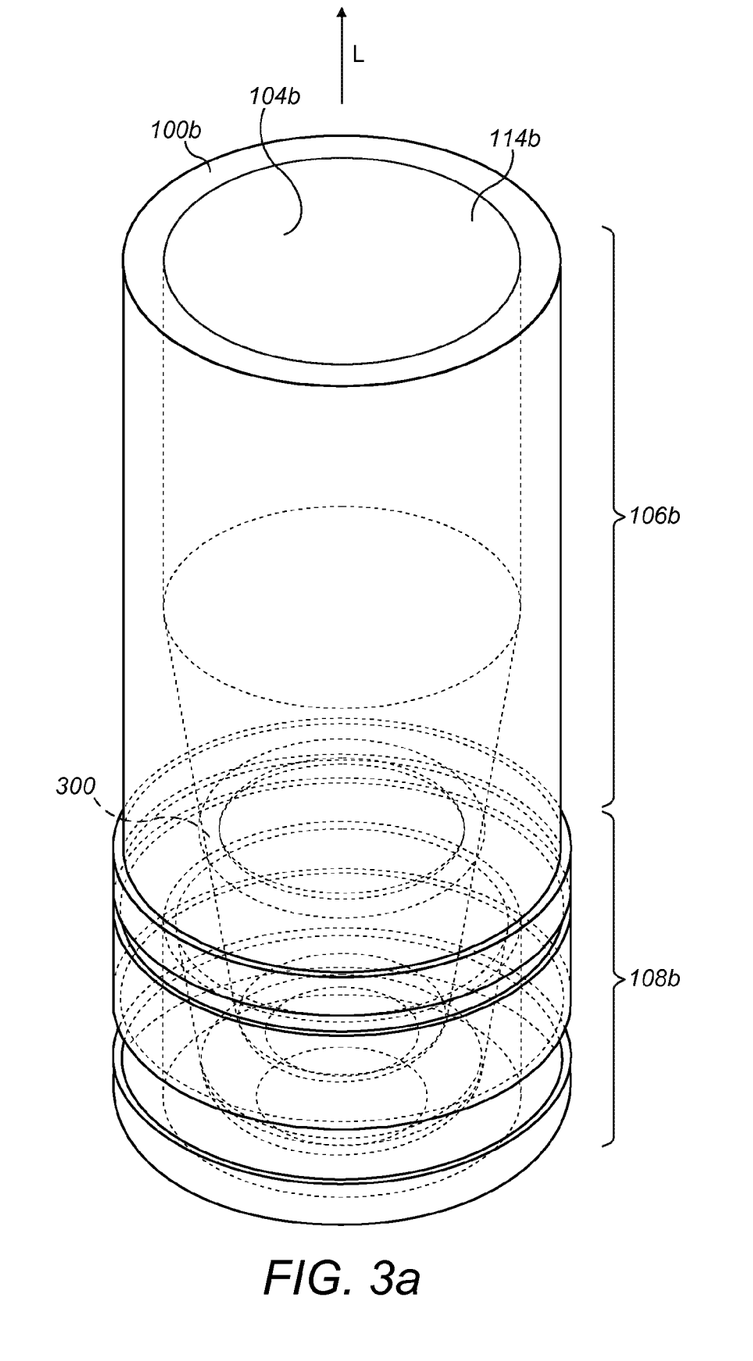
FIG. 3a shows a perspective view of a container for holding a freeze-dried material comprising a biological sample according to a first embodiment of the present invention.
Figure 3B:
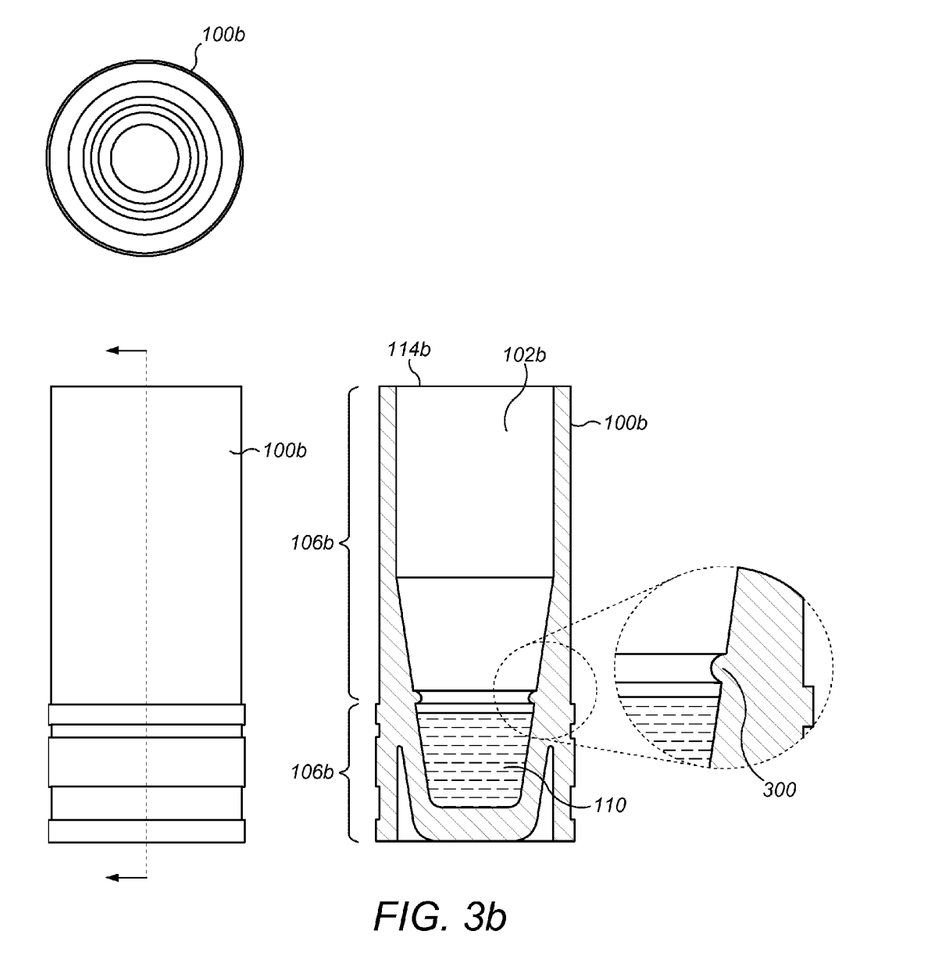
FIG. 3b shows orthographic projections of a container holding a freeze-dried material comprising a biological sample according the first embodiment.

FIGS. 3a and 3b show an embodiment of the present invention in which the tube 100b comprises a stop in the form of a collar 300 extending inwards from the wall 104b of the chamber 102b. FIG. 3a shows the tube 100b prior to insertion of the biological sample. As was described above in relation to FIGS. 2a and 2b, the tube 100b is initially open at a first end 114b, from which the upper portion 106b extends.

During preparation, a material (typically in liquid form) containing the biological sample, is inserted into the chamber 102b via the first end 114b and allowed to accumulate in the lower portion 108b. A freeze-drying process is then performed so that the material coagulates in the lower portion 108b, below the collar 300, thereby forming the cake 110 shown in FIG. 3b, the cake 110 being bonded to the wall 104b of the chamber 102b.

The cake 110 is formed in the lower portion 108b below the collar 300 such that it has a larger external diameter than the internal diameter of the collar 300. In this way, the cake 110 is inhibited from moving through the aperture formed by the collar 300 and is kept in the lower portion 108b of the tube 100b. Thus, the position of the collar 300 defines the boundary between the upper portion 106b and the lower portion 108b, and the volume of the lower portion 108b within which the cake 110 is held. When the biological sample is subsequently reconstituted, by inserting, for example, water into the tube 100b, provided that sufficient volume of water is inserted to fill the tube 100b up to or higher than the level of the collar 300, it can be ensured that substantially all of the cake 110 is dissolved in the water.

The first end 114b may be sealed, subsequent to insertion of the material that is to be freeze-dried with a seal as described above in relation to FIGS. 2a and 2b.

Typically, the collar 300 comprises a substantially semicircular rib with a radius of 0.24 mm running parallel to, and 4.2 mm above, the base of the chamber 102b of the tube 100b.

The collar 300 described in this example is integrally formed with the wall 104b of the tube 100b. However, in some embodiments, a collar is provided by a separate component which is inserted into the tube 100b. This separate component may take the form of a ring, and may be held in place by an interference fit. The position separate component within the tube may be adjustable, allowing adjustment of the boundary between the upper portion 106b and the lower portion 108b of the chamber 102b and, therefore, the volume of the lower portion 108b.

Figure 4:
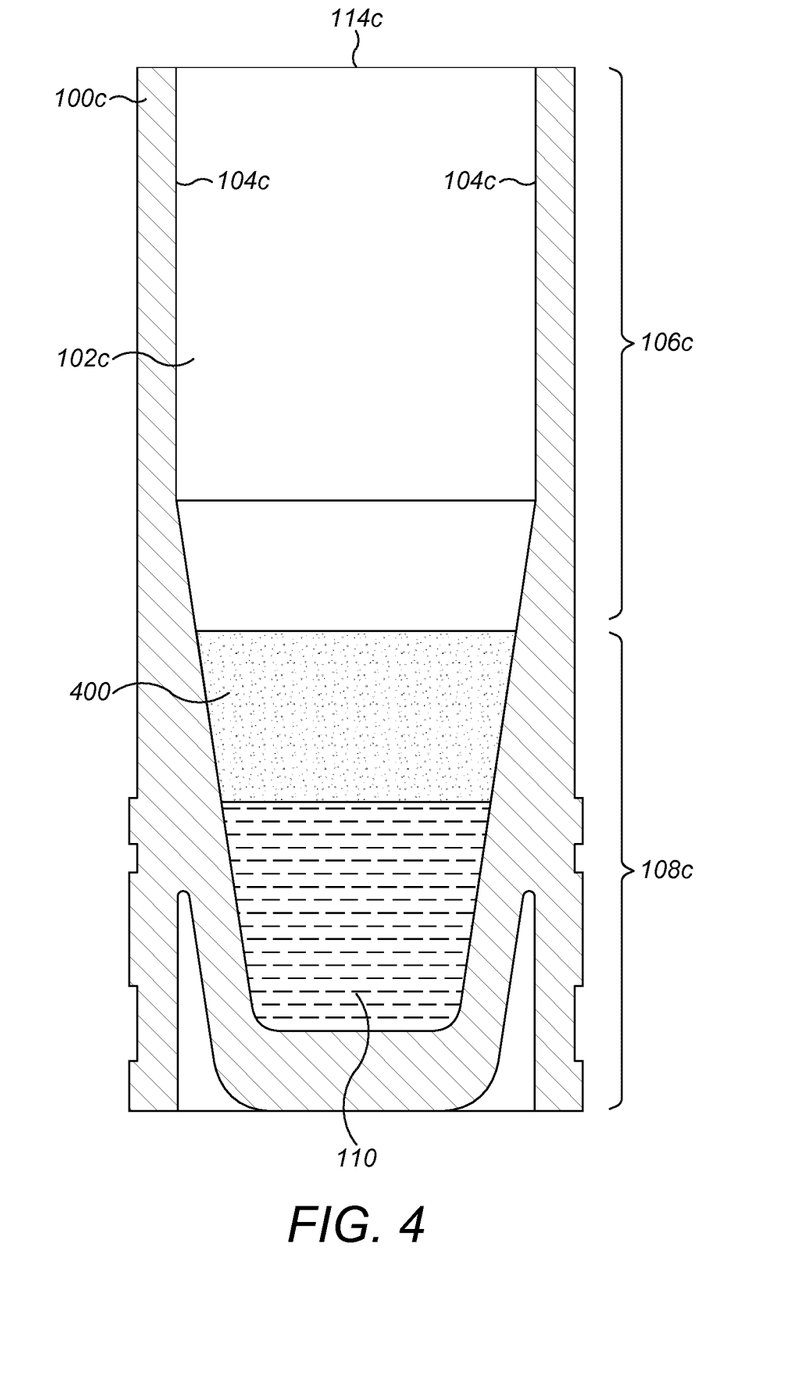
FIG. 4 shows a perspective view of a container for holding a freeze-dried material comprising a biological sample according to a second embodiment of the present invention.

In one embodiment, shown in FIG. 4, rather than using a physical structure 112 to inhibit movement of the cake, the surface of the internal walls 104c of the lower portion 108c of a tube 100c comprises a textured portion 400 to improve the adhesion of the freeze-dried cake 110 onto the internal walls 104c of the tube 100c. The textured portion 400 effectively increases the contact area between the freeze-dried cake 110 and the wall 104 of the tube 100c. The textured portion 400 may comprise a regular pattern of surface features, such as a knurled surface, or may comprise a rough surface with randomly varying surface features. The additional adhesion provided by the increased surface area increases the force required to detach the cake 110 from the tube 100c and, therefore, reduces the likelihood of detachment. The cake 110 may be formed using a freeze-drying process as described above in relation to FIGS. 2a to 3b.

In this embodiment no other physical structures 112 are present in the lower portion 108c of the tube 100c and the freeze-dried cake 110 is held in place solely by adhesion to the interior walls of the tube 100c. However, it will be understood that the textured portion 400 may be used in combination with any of the physical structures 200, 300 in the embodiments described above, or indeed with any other form of physical structure for inhibiting the freeze-dried material from moving from the lower portion 108 of the chamber 102 to the upper portion 106 of the chamber 102. For example, the fins 200 described above in relation to FIGS. 2a and 2b may themselves be textured in order to further increase the strength of the bond between the cake and the fins 200; in the embodiment described above in relation to FIGS. 3a and 3b, the textured portion could be positioned in the lower portion 108b below the collar 300.

Figure 5A:
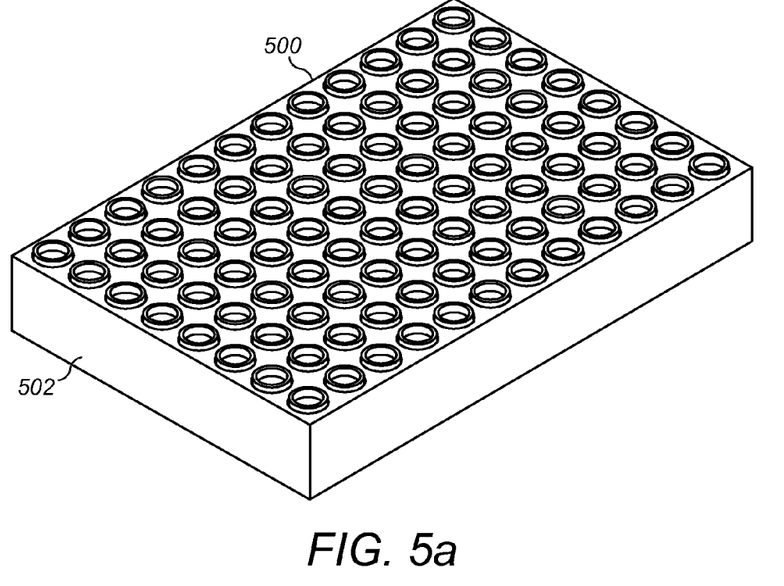
FIG. 5a shows a perspective view of an array of containers for holding a freeze-dried material comprising a biological sample according to embodiments of the present invention.

Any of the tubes 100 described above may be used as individual containers or may be arranged, as in FIG. 5a, in an array 500 for subsequent parallel or batch processing. In the embodiment shown, the tubes 100 are arranged in an 8×12 rectangular array on a base plate 502 with external dimensions corresponding to the SBS industrial standard footprint. Typically, the base plate 502 is 127.76 mm long and 85.48 mm wide.

Figure 5B:
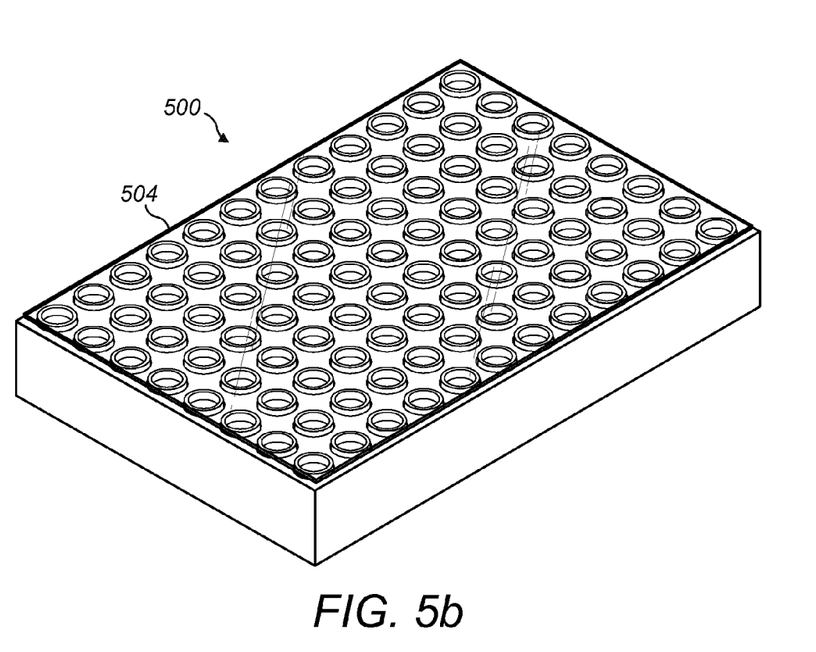
FIG. 5b shows a perspective view of an array of containers for holding a freeze-dried material comprising a biological sample according to embodiments of the present invention.

The array 500 may comprise an impermeable seal 504, which covers the open first ends 114 of each of the tubes 100 as shown in FIG. 5b. In this example, the seal 504 may comprise a continuous sheet in contact with each of the tubes 100; alternatively, the tubes could be individually sealed, as described above. The seal 504 may be held in place with a permanent or semi-permanent adhesive. The seal 504 may be made from a flexible foil/polymer laminate or any other suitable material. The seal 504 may be penetrated by a dispensing needle or removed from the tubes 100 prior to use by breaking the semi-permanent adhesive bond.

Figure 5C:
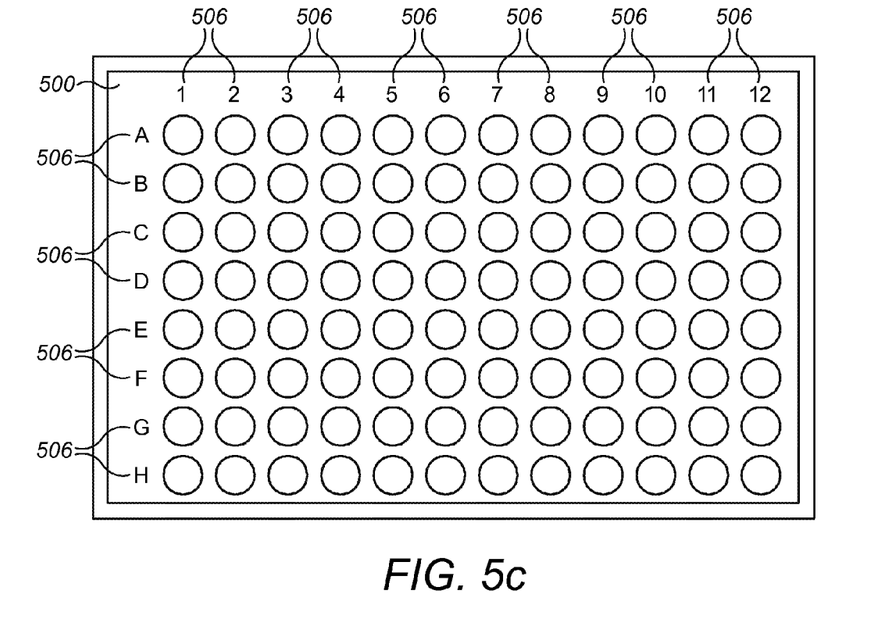
FIG. 5c shows a plan view of an array of containers for holding a freeze-dried material comprising a biological sample according to embodiments of the present invention.

The base plate 502 of the array 500 may comprise identifying grid-coordinates 506, as shown in FIG. 5c, correlating with the positions of each of the tubes 100 to enable identification and addressing of individual samples.

Figure 5D:
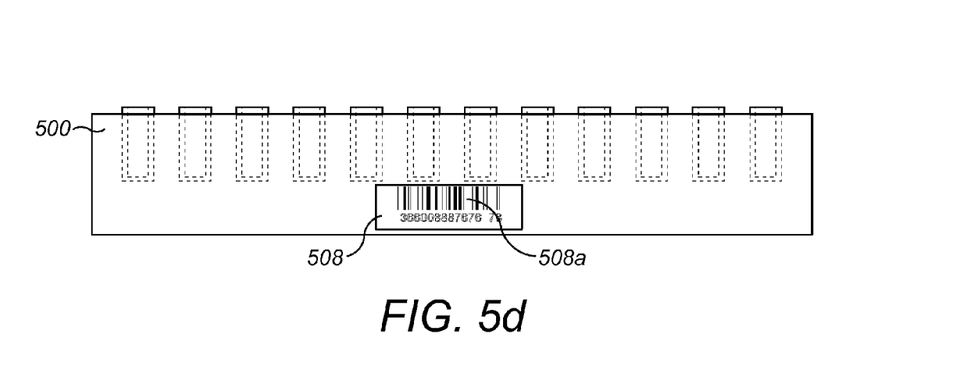
FIG. 5d shows a side view of an array of containers for holding freeze-dried biological samples according to embodiments of the present invention.

The base plate 502 of the array 500 may comprise an identification tag 508 comprising coded computer readable identification information, as shown in FIG. 5d. The tag 508 may comprise a barcode 508a that can be scanned and compared with a database of sample identification codes; other types of tag 508 may be used, for example an RFID tag.

Crush ribs may be added to the external walls of the tube 100 to increase the structural strength of the tube 100 without increasing the overall external dimensions of the tube 100.

The tube 100 and array 500 may comprise a chemically and biologically inert material that can withstand temperatures in the range −40° C. to 50° C. or more. Suitable materials include polycarbonate, polystyrene, or polypropylene. The tube 100 may be manufactured using an injection moulding process or by any other appropriate method. The array 500 may be manufactured as a single component using an injection moulding process or the tubes 100 and the base plate 502 may be manufactured as discrete parts and assembled and fixed together by, for example, an ultrasonic weld or by any other appropriate method.

Figure 6A:
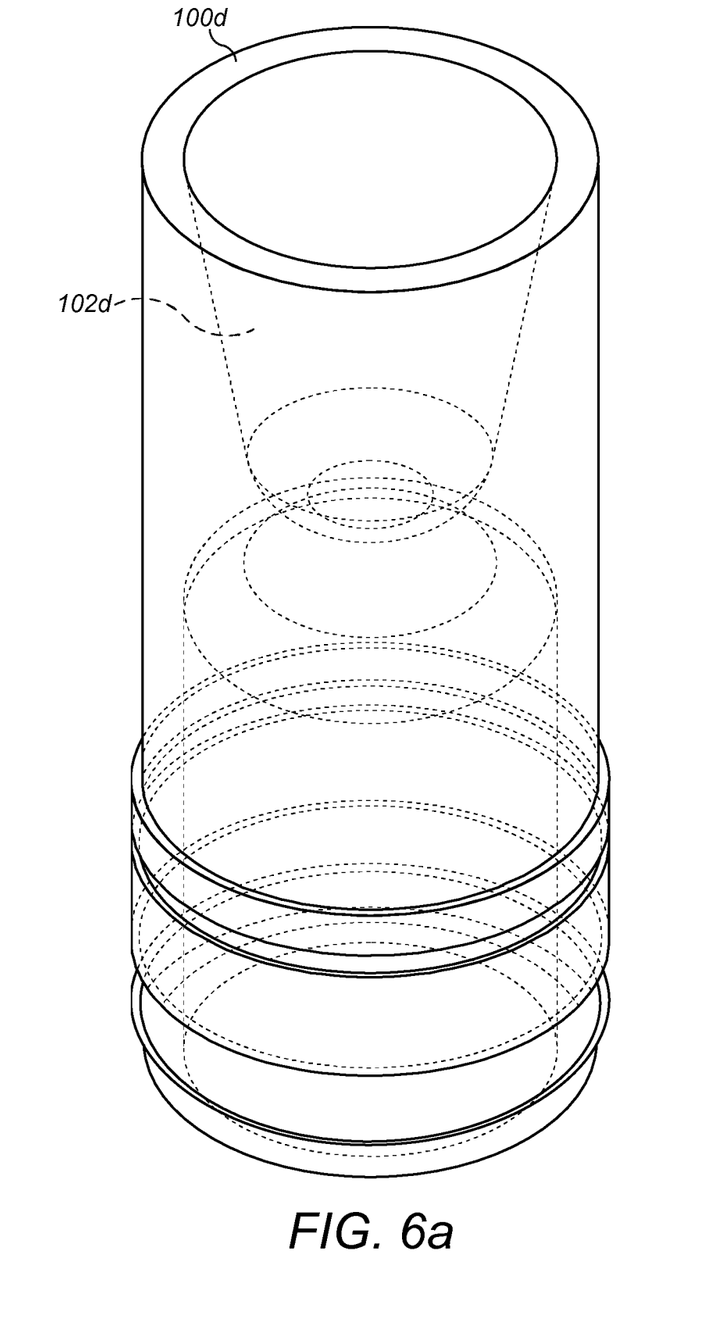
FIG. 6a shows a perspective view of an alternative arrangement in which there is no physical structure holding a freeze-dried material comprising a biological sample.
Figure 6B:
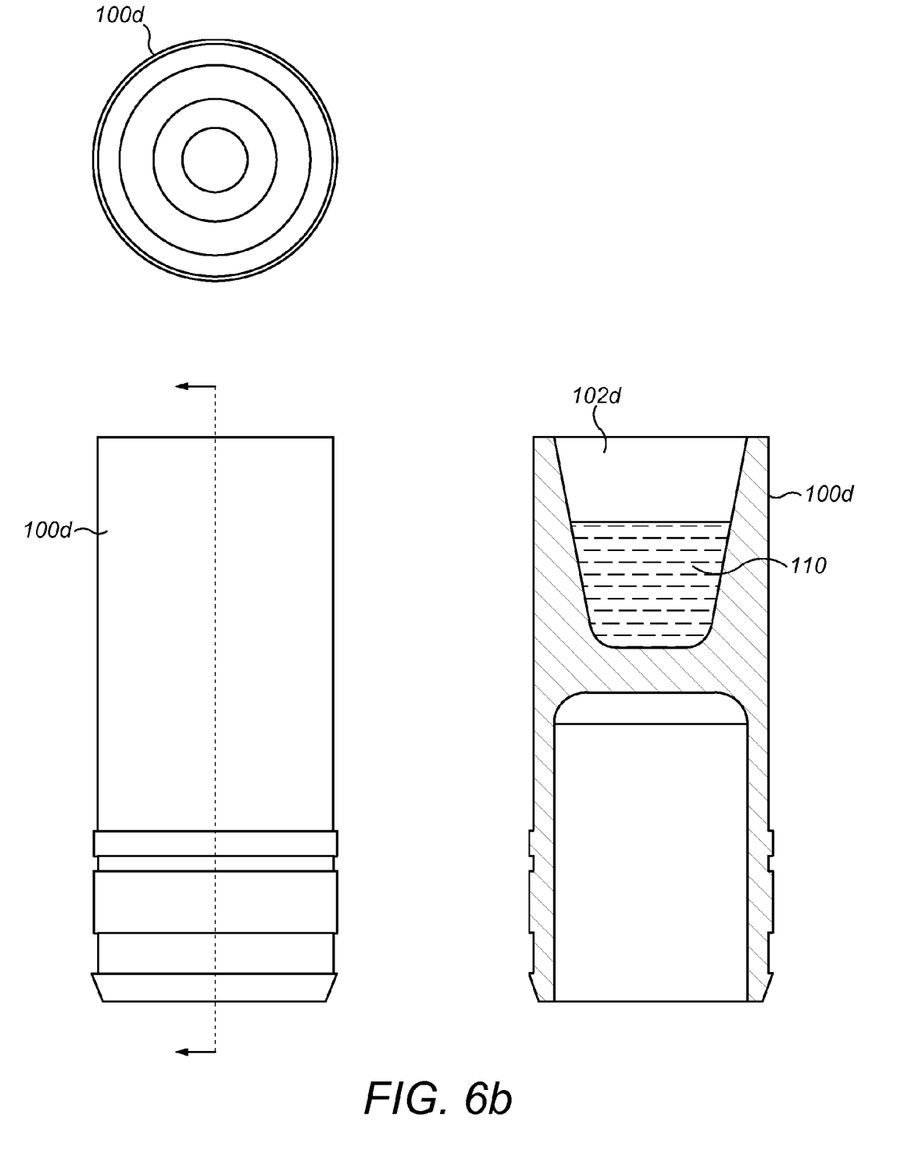
FIG. 6b shows an orthographic projection of an alternative arrangement in which there is no physical structure holding a freeze-dried material comprising a biological sample.

FIGS. 6a and 6b show an alternative tube 100d in which no physical structure 112 inhibits movement of the cake 110. In this arrangement, the tube has a chamber 102d having a volume arranged to be significantly lower than the external volume of a tube 100d but not significantly larger than the volume of liquid required to reconstitute the cake 110. This allows the external dimensions of the tube 100d to be arranged to, for example, satisfy an industry standard, but the internal volume 102d to be reduced, thereby reducing the volume within which the cake 110 can move. Typically, while the external length of the tube 100d remains at 18.3 mm, the internal depth of the tube 100d is reduced to 6.9 mm. The effect of this is to reduce the risk of the freeze-dried cake 110 occupying a volume that is not subsequently filled with a liquid during subsequent reconstitution of the biological material (for example, an enzyme). It will be understood that this arrangement may be used as an individual container or in an array 500, as described above.

Embodiments of the present invention are typically to be used for DNA or RNA amplification procedures such as polymerase chain reaction (PCR) that have common application in a variety of fields including molecular biology, medicine and forensic science.

The above embodiments are to be understood as illustrative examples of the invention. Further embodiments of the invention are envisaged. For example, although in the embodiment described above with reference to FIGS. 2a and 2b, there is no physical indication of a boundary between the lower portion 108b and the upper portion 106b, in some embodiments an indication of the boundary may be provided, for example in the form of a mark or protrusion on the wall 104b of the chamber 114b.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A container storing a freeze-dried material comprising a biological sample, the container comprising a chamber having an upper portion and a lower portion, the chamber comprising a wall and the lower portion being fluidly connected to the upper portion such that, when liquid is received at the upper portion, the received liquid can pass to and accumulate in the lower portion,
wherein the freeze-dried material is located in said lower portion, and the container comprises a physical structure protruding inwards from the wall, the physical structure being for inhibiting the freeze-dried material from moving from the lower portion of the chamber to the upper portion of the chamber,
wherein the freeze-dried material defines a first cross-section and the physical structure comprises a stop extending inwards from an internal wall of said chamber, thereby defining a second cross-section, the second cross-section having a dimension smaller than a corresponding dimension of the first cross-section, and
wherein the biological sample is an enzyme configured for nucleic acid amplification.

2. The container of claim 1, wherein the stop defines a boundary between the upper portion of the chamber and the lower portion of the chamber.

3. The container of claim 2, wherein the stop comprises a movable insert, the movable insert being movable within said chamber, thereby varying said boundary.

4. The container of claim 1, wherein the stop comprises a collar integrally formed with said chamber.

5. The container of claim 1, wherein said physical structure comprises a textured surface.

6. The container of claim 5, further comprising a plurality of fins extending inwards from the wall of the chamber.

7. The container of claim 1, wherein the container is of a plastics material.

8. The container of claim 1, wherein the chamber has a substantially circular cross-section.

9. The container of claim 1, wherein said upper portion extends from a first end of the container, and the container comprises a seal at the first end.

10. The container of claim 1, wherein the enzyme is a polymerase.

11. An apparatus storing a freeze dried material comprising a biological sample, the apparatus comprising:
a plurality of containers according to any preceding claim; and
a base plate supporting the plurality of containers.

12. The apparatus of claim 11, wherein the base plate is of a plastics material.

13. A method of storing a biological sample, comprising:
providing a container, the container comprising a chamber having an upper portion and a lower portion, the chamber having a wall and the lower portion being fluidly connected to the upper portion such that, when liquid is received at the upper portion, the received liquid can pass to and accumulate in the lower portion;
inserting a material containing a biological sample into the chamber and accumulating the material in the lower portion of the chamber; and
performing a freeze-drying process on the material, whereby a freeze-dried material comprising said biological sample is formed in the lower portion,
wherein the container comprises a physical structure protruding inwards from the wall, the physical structure being for inhibiting the freeze-dried material from moving from the lower portion to the upper portion,
wherein the freeze-dried material defines a first cross-section and the physical structure comprises a stop extending inwards from an internal wall of said chamber, thereby defining a second cross-section, the second cross-section having a dimension smaller than a corresponding dimension of the first cross-section, and
wherein the biological sample is an enzyme configured for nucleic acid amplification.

14. The method of claim 13, wherein the enzyme is a polymerase.

15. The method of claim 13, wherein the container further comprises a plurality of fins extending inwards from the wall of the chamber, and wherein the plurality of fins and the physical structure comprise a textured surface.

16. A container storing a freeze-dried material comprising a biological sample, the container comprising a chamber having an upper portion and a lower portion, the chamber comprising a wall and the lower portion being fluidly connected to the upper portion such that, when liquid is received at the upper portion, the received liquid can pass to and accumulate in the lower portion,
wherein the freeze-dried material is located in said lower portion, and the wall in said lower portion comprises a rough surface to which the freeze-dried material is bonded, whereby the freeze-dried biological sample is prevented from moving from the lower portion to the upper portion, and wherein the biological sample is an enzyme configured for nucleic acid amplification.

17. The container of claim 16, wherein the enzyme is a polymerase.

* * * * *